United States Patent
Kim et al.

[11] Patent Number: 5,848,113
[45] Date of Patent: Dec. 8, 1998

[54] COATED ELECTROCHEMICAL CORROSION POTENTIAL SENSOR

[75] Inventors: Young Jin Kim, Clifton Park; Peter Louis Andresen, Schenectady; Dennis Michael Gray, Delanson, all of N.Y.

[73] Assignee: General Electric Company, Schenectady, N.Y.

[21] Appl. No.: 928,112

[22] Filed: Sep. 12, 1997

[51] Int. Cl.⁶ .................. G21C 17/10; G01N 27/30
[52] U.S. Cl. .................. 376/305; 376/245; 376/249; 376/256; 204/400; 204/435
[58] Field of Search .................. 376/305, 245, 376/249, 256; 204/400, 435; 205/775.5, 794.5; 324/446, 449

[56] References Cited

U.S. PATENT DOCUMENTS

| | | | |
|---|---|---|---|
| 4,978,921 | 12/1990 | Indig et al. | 324/446 |
| 4,990,855 | 2/1991 | Niedrach et al. | 324/449 |
| 5,043,053 | 8/1991 | Indig et al. | 204/421 |
| 5,118,913 | 6/1992 | Taylor | 204/435 |
| 5,192,414 | 3/1993 | Indig et al. | 204/400 |
| 5,203,984 | 4/1993 | Sakai et al. | 204/435 |
| 5,217,596 | 6/1993 | Indig et al. | 204/435 |
| 5,465,281 | 11/1995 | Andresen et al. | 376/305 |
| 5,571,394 | 11/1996 | Hettiarachchi et al. | 204/400 |

OTHER PUBLICATIONS

"Electrochemical Sensors for Application to Boiling Water Reactors," ME Indig, Citations from Energy Science and Technology, (DOE): EDB ISS 94–13,94:08747 94001033757, pp. 4224–4236.

*Primary Examiner*—Charles T. Jordan
*Assistant Examiner*—Matthew J. Lattig
*Attorney, Agent, or Firm*—Noreen C. Johnson; Douglas E. Stoner

[57] ABSTRACT

An electrochemical corrosion potential sensor includes a sensor tip electrically joined to a conductor, and a ceramic insulator joined to the tip around the conductor. A sleeve is joined to the insulator around the conductor, and is electrically insulated from the tip by the ceramic insulator. The insulator has an exposed surface axially separating the tip and sleeve, and a ceramic coating is bonded thereto for preventing dissolution of the insulator by reactor water. In a preferred embodiment, the ceramic insulator is sapphire, and the ceramic coating is yttria-stabilized-zirconia or magnesia-stabilized-zirconia which may be plasma sprayed over the insulator.

10 Claims, 2 Drawing Sheets

COATED ELECTROCHEMICAL CORROSION POTENTIAL SENSOR

BACKGROUND OF THE INVENTION

The present invention relates generally to nuclear reactors, and, more specifically, to electrochemical corrosion potential sensors therein.

A nuclear power plant includes a nuclear reactor for heating water to generate steam which is routed to a steam turbine which extracts energy therefrom for powering an electrical generator to produce electrical power. The nuclear reactor is typically in the form of a boiling water reactor having suitable nuclear fuel disposed in a reactor pressure vessel in which water is heated.

The water and steam are carried through various components and piping which are typically formed of stainless steel, with other materials such as alloy 182 weld metal and alloy 600 being used for various components directly inside the reactor pressure vessel.

It has been found that these materials tend to undergo intergranular stress corrosion cracking depending on the chemistry of the material, degree of sensitization, the presence of tensile stress, and the chemistry of the reactor water. By controlling any one or more of these critical factors, it is possible to control the propensity of a material to undergo intergranular stress corrosion cracking.

However, it is conventionally known that intergranular stress corrosion cracking may be controlled or mitigated by controlling a single critical parameter called the electrochemical corrosion potential of the material of interest. Thus, considerable efforts have been made in the past decade to measure the electrochemical corrosion potential of the materials of interest during the power operation of the reactor. This, however, is not a trivial task because the electrochemical corrosion potential of the material varies depending on the location of the material in the reactor circuit.

As an example, a material in the reactor core region is likely to be more susceptible to irradiation assisted stress corrosion cracking than the same material exposed to an out-of-core region. This is because the material in the core region is exposed to the highly oxidizing species generated by the radiolysis of water by both gamma and neutron radiation under normal water chemistry conditions, in addition to the effect of direct radiation assisted stress corrosion cracking. The oxidizing species increases the electrochemical corrosion potential of the material which in turn increases its propensity to undergo intergranular stress corrosion cracking or irradiation assisted stress corrosion cracking.

Thus, a suppression of the oxidizing species is desirable in controlling intergranular stress corrosion cracking. An effective method of suppressing the oxidizing species coming into contact with the material is to inject hydrogen into the reactor water via the feedwater system so that recombination of the oxidants with hydrogen occurs within the reactor circuit. This results in an overall reduction in the oxidant concentration present in the reactor which in turn mitigates intergranular stress corrosion cracking of the materials, if the oxidant concentration is suppressed to very low levels.

This method is conventionally called hydrogen water chemistry, which is widely practiced for mitigating intergranular stress corrosion cracking of materials in boiling water reactors. When hydrogen water chemistry is practiced in a boiling water reactor, the electrochemical corrosion potential of the stainless steel material decreases from a positive value generally in the range of 0.050 to 0.200 V(SHE) under normal water chemistry to a value less than −0.230 V(SHE), where SHE stands for the Standard Hydrogen Electrode potential. There is considerable evidence that when the electrochemical corrosion potential is below this negative value, intergranular stress corrosion cracking of stainless steel can be mitigated and the intergranular stress corrosion cracking initiation can be prevented.

Thus, considerable efforts have been made in the past decade to develop reliable electrochemical corrosion potential sensors to be used as reference electrodes which can be used to determine the electrochemical corrosion potential of operating surfaces. These sensors have been used in more than a dozen boiling water reactors worldwide, with a high degree of success, which has enabled the determination of the minimum feedwater hydrogen injection rate required to achieve electrochemical corrosion potential sensors of reactor internal surfaces and piping below the desired negative value.

However, the sensors have a limited lifetime in that some have failed after only three months of use while a few have shown evidence of successful operation for approximately six to nine months. Only one sensor has shown successful operation over a period of one fuel cycle, e.g. eighteen months in a US boiling water reactor.

Recent experience with two boiling water reactors in the United States has shown that the two major modes of failure have been cracking and corrosive attack in the ceramic-to-metal braze used at the sensing tip, and the dissolution of sapphire insulating ceramic material used to electrically isolate the sensing tip from the metal conductor cable for platinum or stainless steel type sensors.

The electrochemical corrosion potential sensors may be mounted either directly in the reactor core region for directly monitoring electrochemical corrosion potential of in-core surfaces, or may be mounted outside the reactor core to monitor the electrochemical corrosion potential of out-of-core surfaces. However, the typical electrochemical corrosion potential sensor nevertheless experiences a severe operating environment in view of the high temperature of water well exceeding 88° C.; relatively high flowrates thereof up to and exceeding several m/s; and due to the high nuclear radiation in the core region. This complicates the design of the sensor since suitable materials are required for this hostile environment, and must be suitably configured for providing a water-tight assembly for a suitable useful life.

As indicated above, experience with the typical platinum electrochemical corrosion potential sensor has uncovered shortcomings thereof leading to premature failure before expiration of a typical fuel cycle. Accordingly, it is desired to improve the design of electrochemical corrosion potential sensors for improving the useful life thereof for achieving the goal of a one or more fuel cycle life.

SUMMARY OF THE INVENTION

An electrochemical corrosion potential sensor includes a sensor tip electrically joined to a conductor, and a ceramic insulator joined to the tip around the conductor. A sleeve is joined to the insulator around the conductor, and is electrically insulated from the tip by the ceramic insulator. The insulator has an exposed surface axially separating the tip and sleeve, and a ceramic coating is bonded thereto for preventing dissolution of the insulator by reactor water. In a preferred embodiment, the ceramic insulator is sapphire, and the ceramic coating is yttria-stabilized-zirconia or magnesia-stabilized-zirconia which may be plasma sprayed over the insulator.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
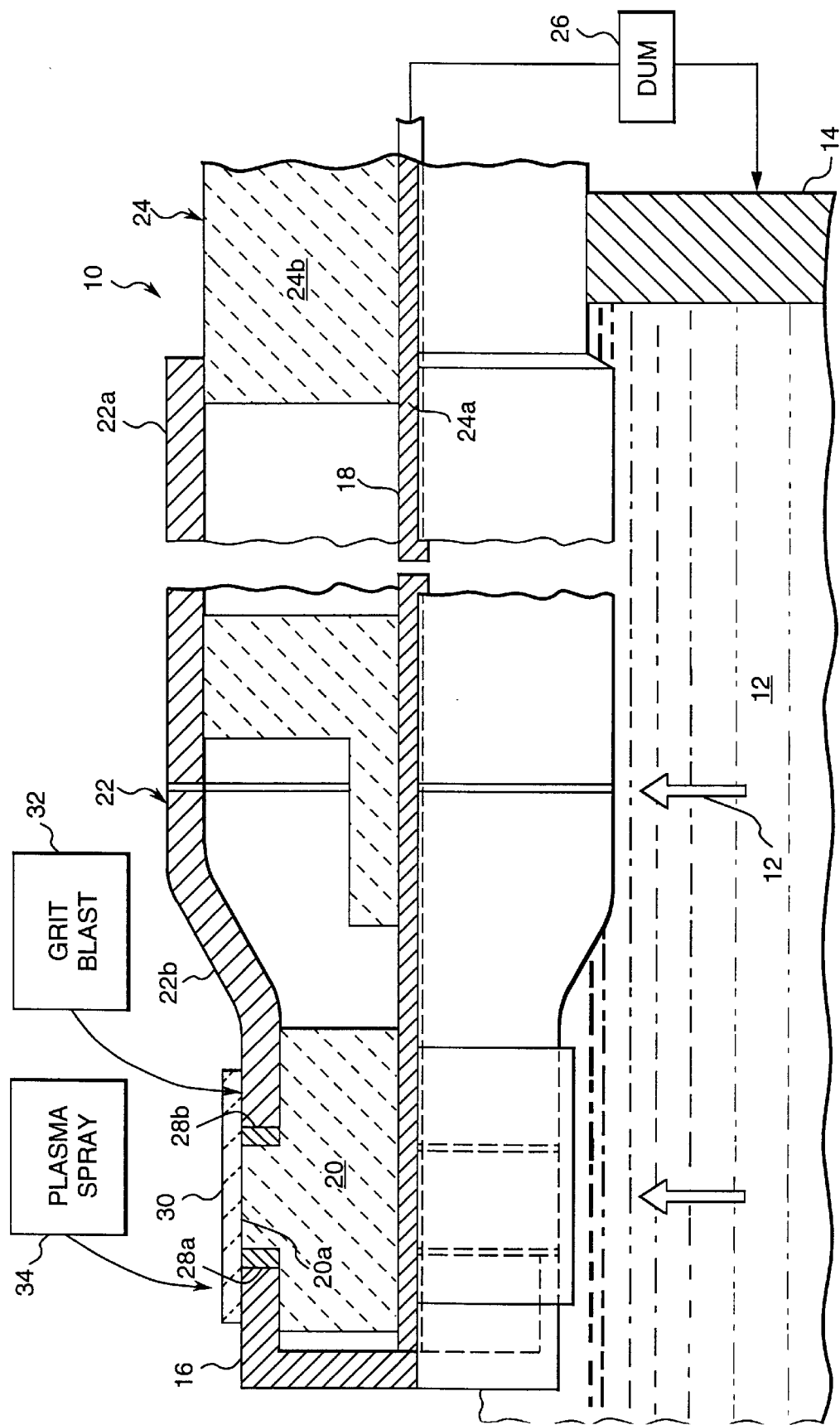
FIG. 1 is a schematic representation of an electrochemical corrosion potential sensor in accordance with one embodiment of the present invention having a ceramic coating plasma sprayed over a ceramic insulator thereof.

Illustrated schematically in FIG. 1 is a sensor 10 configured for measuring electrochemical corrosion potential of reactor surfaces in circulating water 12 inside the pressure vessel of a conventional boiling water nuclear reactor 14, shown in relevant part. The sensor 10 includes a sensor tip 16 suitably electrically joined to a central conductor 18. The sensor tip 16 may have any suitable configuration such as a cylindrical plug or tubular cup formed of a suitable noble metal such as platinum or stainless steel.

A tubular ceramic electrical insulator 20 is suitably joined at one end to the tip 16 around the conductor 18. A tubular transition sleeve 22 is suitably joined to the insulator 20 at an opposite end thereof, also around the conductor 18, and is electrically insulated from the tip 16 by the ceramic insulator 20.

In the exemplary embodiment illustrated in FIG. 1, the transition sleeve 22 includes a first portion 22a of suitable length suitably joined to a second portion 22b to which the ceramic insulator 20 is directly attached. The first portion 22a may be formed of stainless steel welded to the second portion 22b, which is formed of a conventional material such as Kovar, an iron-nickel-cobalt material, or from Invar also known as alloy 42, which is an iron-nickel material without cobalt for eliminating irradiation thereof during use in the boiling water reactor. The ceramic insulator 20 is preferably formed of sapphire.

The sensor 10 is joined to a suitable mineral oxide insulating conducting cable 24 which electrically joins the sensor tip 16 to a conventional device or digital voltmeter 26 for measuring electrochemical corrosion potential in volts. The cable 24 typically includes a central conductor 24a, which may be stainless steel, spot welded to the tip conductor 18, and an outer electrically insulating sheath 24b of suitable mineral oxide ceramic for example.

In practice, a plurality of suitable electrochemical corrosion potential sensors are used in the boiling water reactor 14. The sensors are suitably mounted in the boiling water reactor, and for example, may extend through a pressure vessel wall for monitoring electrochemical corrosion potential of in-core surfaces in the water 12 circulating through the reactor core. The sensor 10 is, therefore, subject to a high nuclear radiation environment, with elevated water temperature greater than 100° C., and with substantial water flowrates which can exceed 1 m/s.

The various components of the sensor 10 must be suitably sealed to prevent leakage of the water 12 therein. For example, the ceramic insulator 20 is typically joined to the tip 16 and the sleeve 22 at corresponding ceramic-to-metal first and second brace joints 28a,b. The joints 28a,b are effected by conventional brazing which occurs at an elevated temperature such as about 940° C. In order to reduce the likelihood of undesirable cracking between the ceramic insulator 20 and the tip 16 and sleeve 22, the materials thereof have suitable coefficients of thermal expansion generally similar to that of the ceramic insulator 20 for reducing differential thermal expansion and contraction thereof during the brazing process. For the sleeve 22, the Kovar or alloy 42 material provides this advantage; and for the tip 16, platinum is typically used.

The ceramic insulator 20 extends in part from both of its opposite ends into the tip 16 and the sleeve 22, with a central exposed annular surface 20a axially separating the tip 16 and sleeve 22.

The electrochemical corrosion potential sensor 10 described above is conventional in configuration and operation and may include various other components as desired for providing a suitable sensor for measuring electrochemical corrosion potential within the boiling water reactor 14 in which it is mounted.

As indicated above in the Background section, the sapphire insulator 20 is exposed in a hostile environment of high radiation, high temperature water, and relatively high flowrates thereof. Experience has shown that a fundamental failure mode of the sensor 10 occurs by a rapid dissolution of the sapphire insulator 20 which ablates away over time. In accordance with the present invention, the sensor 10 is modified for improving its useful life and protecting the sapphire insulator 20 from dissolution.

More specifically, a suitable ceramic coating 30 is bonded to the exposed surface 20a and overlaps adjoining portions of the tip 16 and sleeve 22 for preventing dissolution of the insulator 20 by the circulating water 12 in the reactor. The coating 30 preferably extends also over the first and second braze joints 28a,b for also protecting them and providing a redundant seal thereat. The additional ceramic electrically insulating coating 30 provides an effective barrier layer atop the otherwise exposed sapphire insulator 20. In a preferred embodiment, the coating 30 is yttria-stabilized-zirconia or magnesia-stabilized-zirconia for its ability to withstand the high temperature, high flow water, under high radiation environment.

In one embodiment of the improved sensor 10 illustrated in FIG. 1, a 7 mil (0.178 mm) thickness layer of the yttria-stabilized-zirconia coating 30 was successfully prepared atop the sapphire insulator 20 and first and second braze joints 28a,b. The coating 30 was also sprayed to overlap adjacent portions of the tip 16 and sleeve 22.

As shown schematically in FIG. 1, a conventional grit blasting device 32 was initially used to grit blast the exposed sapphire surface and adjoining metal surfaces for suitably roughening those surfaces prior to plasma deposition. A conventional plasma spraying device 34 was then used for plasma spraying the ceramic coating 30 across the roughened surfaces to bond the coating 30 thereto. Visual examination of the cross section morphology of the yttria-stabilized-zirconia layer coating 30 atop the sapphire insulator 20 revealed direct bonding therebetween.

The exemplary yttria-stabilized-zirconia-coated sensor 10 was tested in a water environment at about 288° C. with various water chemistry conditions by cycling the normal water chemistry (200 ppb $O_2$) and hydrogen water chemistry (150 ppb $H_2$) for about four months at a low flowrate of a few cm/s, and for about two months at high flowrate of about 1.5 m/s. The yttria-stabilized-zirconia layer was periodically inspected every two weeks. No weight loss, no significant degradation of the yttria-stabilized-zirconia coating, and no impedance change (greater than 60 Kohm at 288° C.) were observed during testing. Accordingly, the yttria-stabilized-zirconia coated sensor 10 enjoys improved resistance to high flowrate water for shielding the sapphire insulator 20 against dissolution.

In the preferred embodiment illustrated in FIG. 1, the plasma spraying of the coating 30 is effected at a temperature suitably less than the temperature for brazing the joints 28a,b to prevent damage thereto. Typical brazing temperatures are about 940° C., whereas a suitable plasma spraying temperature may be about 600° C.

Figure 2:
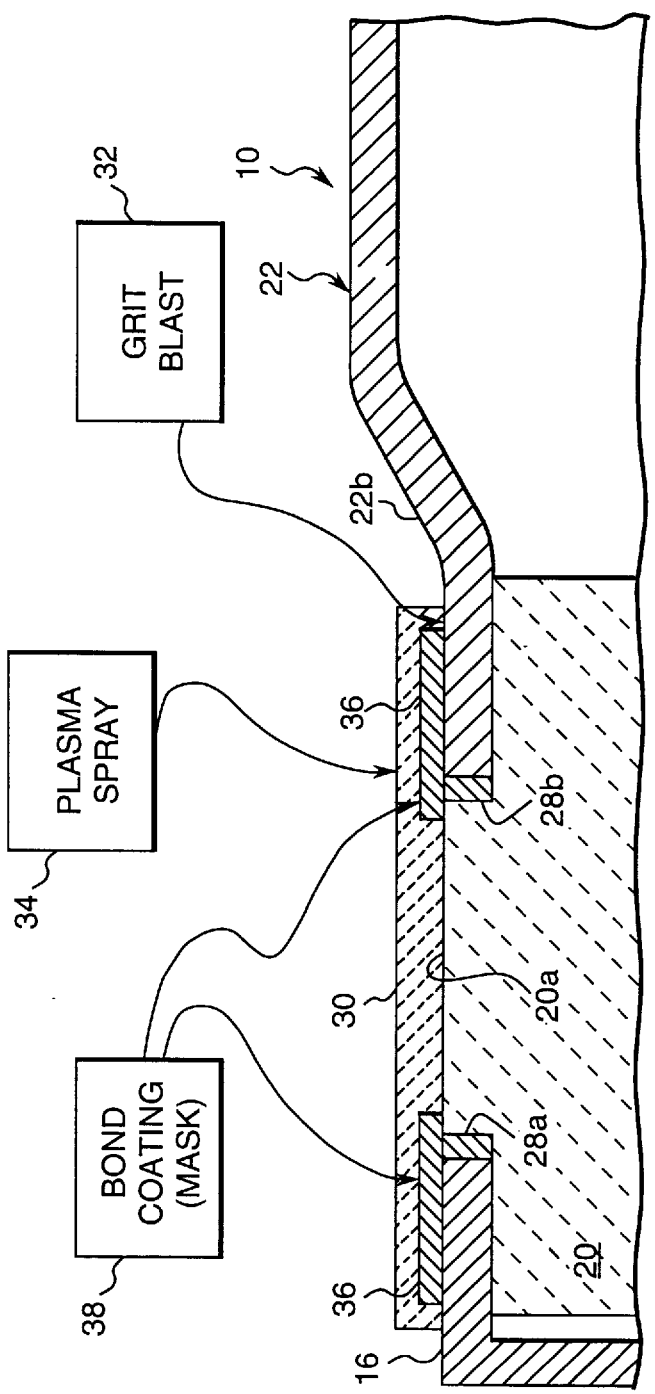
FIG. 2 is a schematic representation of a tip portion of the electrochemical corrosion potential sensor illustrated in FIG. 1 in accordance with a second embodiment of the present invention including an additional bond coating formed in part between the ceramic coating and exposed surfaces.

In order to improve the bonding of the yttria-stabilized-zirconia coating 30 on the sensor 10, a suitably rough bond coating 36 may be first applied as illustrated in an alternate embodiment of the sensor 10A shown in FIG. 2. The bond coating 36 may have any suitable thickness, for example 5–10 mils (0.127–0.254 mm), and may be made by any suitable coating apparatus 38, which may be a plasma spraying device as well. Typical bond coatings are electrically conducting metal alloys such as Nickel 211, which is a Nickel-Chrome-Iron-Aluminum alloy.

However, the conducting bond coating 36 must be suitably configured to prevent electrical conduction between the tip 16 and the sleeve 22. This may be accomplished by using a suitable mask at an intermediate or center portion of the ceramic insulator 20 at the exposed surface 20a, as illustrated in FIG. 2 prior to the depositing the bond coating 36 for maintaining electrical insulation thereat. The ceramic coating 30 may then be suitably deposited atop the bond coating 36, and atop the intermediate portion of the ceramic insulator 20 directly atop the exposed surface 20a.

The bond coating 36 is, therefore, bonded to selected surfaces including the exposed end portions of the ceramic insulator 20 and the adjoining portions of the tip 16 and sleeve 22 across the first and second braze joints 28a,b. The ceramic coating 30 is, therefore, directly bonded in part to the intermediate portion of the ceramic insulator 20 at the exposed surface 20a, as well as being bonded to the bond coating 36 axially therefrom for maintaining electrical insulation between the tip 16 and sleeve 22.

By plasma spraying the ceramic coating 30 in a suitable vacuum, a relatively high density ceramic coating 30 of about 97% may be obtained. Even some micro-cracks in the yttria-stabilized-zirconia layers are acceptable for purposes of the present invention because the outermost yttria-stabilized-zirconia coating layers will still substantially reduce the flow induced dissolution rate of sapphire.

Accordingly, the improved yttria-stabilized-zirconia coated sensors 10,10A illustrated in FIGS. 1 and 2 provide protection of the sapphire insulator 20 against dissolution in the high temperature and flow condition of the reactor water in a high radiation environment. This results in a corresponding increase in the useful life of the improved sensor, with a relatively simple modification of the conventional design.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims:

What is claimed is:

1. A sensor for measuring electrochemical corrosion potential in a nuclear reactor comprising:

a sensor tip electrically joined to a conductor;

a tubular ceramic insulator joined to said tip around said conductor;

a tubular sleeve joined to said ceramic insulator around said conductor, and electrically insulated from said tip by said ceramic insulator;

said ceramic insulator having an exposed surface axially separating said tip and sleeve; and a ceramic coating bonded to said exposed surface and adjoining portions of said tip and sleeve for preventing dissolution of said ceramic insulator by circulating water in said reactor.

2. A sensor according to claim 1 wherein:

said tip is a noble metal;

said sleeve is a metal;

said ceramic insulator is joined to said tip and sleeve at corresponding ceramic-to-metal braze joints; and said coating extends over said braze joints.

3. A sensor according to claim 2 wherein:

said ceramic insulator is sapphire; and said coating is yttria-stabilized-zirconia or magnesia-stabilized-zirconia.

4. A sensor according to claim 2 further comprising:

a bond coating bonded to said ceramic insulator, tip, and sleeve across said braze joints; and said ceramic coating is in turn bonded atop said bond coating.

5. A sensor according to claim 4 wherein said ceramic coating is directly bonded in part to an intermediate portion of said ceramic insulator at said exposed surface, and bonded to said bond coating axially therefrom for maintaining electrical insulation between said tip and sleeve.

6. A method of fabricating the sensor of claim 1 for improving life thereof in said reactor comprising:

roughening said exposed surface and adjoining surface portions of said tip and sleeve; and plasma spraying said ceramic coating across said roughened surfaces to bond said ceramic coating thereto.

7. A method according to claim 6 wherein said plasma spraying is effected at a temperature less than a temperature for brazing said joints.

8. A method according to claim 7 further comprising:

first depositing a bond coating on said ceramic insulator, tip, and sleeve, across said braze joints; and secondly plasma spraying said ceramic coating atop said bond coat.

9. A method according to claim 8 further comprising:

masking an intermediate portion of said ceramic insulator at said exposed surface prior to depositing said bond coating to maintain electrical insulation thereat; and plasma spraying said ceramic coating atop said bond coating, and atop said intermediate portion directly atop said exposed surface.

10. A method according to claim 9 wherein:

said ceramic insulator is sapphire; and said coating is yttria-stabilized-zirconia or magnesia-stabilized-zirconia.

* * * * *